United States Patent [19]

Cohen et al.

[11] Patent Number: 5,457,316
[45] Date of Patent: Oct. 10, 1995

[54] METHOD AND APPARATUS FOR THE DETECTION AND IDENTIFICATION OF TRACE GASES

[75] Inventors: Martin J. Cohen, West Palm Beach; Robert M. Stimac, Palm Beach Gardens; Roger F. Wernlund, Lake Worth, all of Fla.

[73] Assignee: PCP, Inc., West Palm Beach, Fla.

[21] Appl. No.: 363,762

[22] Filed: Dec. 23, 1994

[51] Int. Cl.[6] .................................................. H01J 49/40
[52] U.S. Cl. ........................... 250/286; 250/282; 250/288
[58] Field of Search .................................... 250/287, 282, 250/286, 288

[56] References Cited

U.S. PATENT DOCUMENTS

| | | | |
|---|---|---|---|
| 4,378,499 | 3/1983 | Spangler et al. | 250/288 |
| 4,390,784 | 6/1983 | Browning et al. | 250/287 |
| 5,032,721 | 7/1991 | Bacon et al. | 250/288 |
| 5,053,343 | 10/1991 | Vora et al. | 250/287 |
| 5,185,523 | 2/1993 | Kitagawa et al. | 250/281 |
| 5,338,931 | 8/1994 | Spangler et al. | 250/287 |

Primary Examiner—James Beyer
Attorney, Agent, or Firm—Schweitzer Cornman & Gross

[57] ABSTRACT

The present invention relates to an ion mobility spectrometer sensor apparatus which is in a hermetically sealed housing, utilizing a drift gas for the determination of trace contaminants in a carrier gas, including a container for a sample gas containing an analyte the concentration of which is to be determined, means for purifying the sample gas to produce the carrier gas from it, the means for purifying being hermetically connected from the container through a metallic pipe, a source for the purified drift gas which may be the same or different than the carrier gas, an ion mobility spectrometer sensor having a carrier gas entrance and a drift gas entrance and a gas exit, the ion mobility spectrometer sensor being hermetically connected by a metallic pipe from the purifying means and from the source of the drift gas, a back diffusion trap is hermetically connected from the gas exit, and a signal readout is electrically and hermetically connected from the ion mobility spectrometer sensor for electrically sensing and displaying signals obtained in the sensor.

19 Claims, 4 Drawing Sheets

METHOD AND APPARATUS FOR THE DETECTION AND IDENTIFICATION OF TRACE GASES

FIELD OF THE INVENTION

The present invention relates to method and apparatus for the detection and identification of trace amounts of gases which heretofore could not be detected in an ion mobility spectrometer (IMS) because of the presence of significant amounts of water vapor or other interferents.

BACKGROUND OF THE INVENTION

Many gases cannot be detected in the IMS because of the presence of water vapor and other interferences normally present in the current state of the art for the IMS instrument. The heretofore undetectable gases in the IMS can now be detected by practicing methods and by using apparatus which will reduce the water vapor and other interferents by the use of purification materials and apparatus described in this invention.

A number of methods are known for the purification of gases. Molecular sieves are porous, inorganic materials which present a large clean, very porous surface that can remove water and organic vapors from a gas stream, mainly by physical adsorption. This porous material operates at room temperature, but it is better and has a larger adsorptive capacity at lower temperatures. It is reactivated by heating in a clean gas stream into which it will give off its adsorbed materials. The molecular sieve has an adsorptive efficiency which is a function of many parameters including the impurities adsorbed.

Activated charcoal works broadly in the same general manner as molecular sieve. It is less efficient with water but adsorbs vapor organics better as in the case of gas masks and the like. Again, adsorption properties for specific materials vary among the charcoals, based on the charcoal source, preparation, activation, recycling, etc.

Cryogenic purification adds cooling of the adsorbent. Reducing the temperatures of the material improves the retention capacity for the impurities where physical adsorption mechanisms are involved.

Getters involve a method of converting a gas to a solid by the use of chemical reaction of the impurity and the getter material. As an example, porous zirconium reacts, when heated, with all materials except rare gases. Thus rare gases (helium, argon, etc.) can be purified. Getters are usually used in a vacuum but since they do not absorb rare gases, they can be used to purify these substances also without vacuum (see for example Handbook of Electron Tube and Vacuum Technique, Rosebury Publ., 1965, p. 105).

One variety of gas chromatograph column is filled with the adsorbing, purifying material (molecular sieve, charcoal, etc.) to form a tube which is elongated as compared to its diameter. An already cleaned rare gas, e.g. helium, is used as the carrier gas in the column. A gas sample is added to the column (as an injection made at the head of the column) which sample can be considered a mixture of the target gas and its impurities. Sorting of the gases occurs wherein the target gases have the shorter retention time and the impurities the longer retention time as they pass through the column. Thus the impurities are removed from the mixture by remaining in the column. The column is cleaned by back flushing with clean gas and venting the impurities. In the present case where water vapors constitute the undesired impurities, the water has the long retention time and remains in the column. In this manner a dry target gas sample exits from the column, and can be introduced into the IMS system.

Selective membranes can also be used for gas purification. These materials utilize differential solubility of vapors in the membrane and/or differential diffusivity of vapors.

There is an increased commercial need for the measurement of gases that are present in trace amounts, typically in concentrations of 100 parts-per-billion and less. Ion mobility spectrometry (also referred to in the prior an as plasma chromatography) is a particularly useful technique for the determination of analyte gases in trace amounts. Typical uses of IMS are is described, among others, in earlier U.S. Pat. Nos. 3,262,180; 3,262,182; 3,593,018; 3,596,088; 3,621,239; 3,621,240; 3,624,389; 3,626,178; 3,626,179; 3,639,757; 3,668,382; 3,668,385; 3,697,748; 3,699,333; 3,742,213; 3,812,355; 3,845,301; 4,195,513; and 5,162,652, and further in U.S. Pat. Nos. 3,262,181;, 3,629,574; and 3,668,383. In IMS the trace chemicals to be detected are ionized and then separated from each other due to their differing drift velocities in an electric field. The time differentials of their arrivals to a collector are then registered. Hence the nomenclature referring to "ion mobility" in the spectrometric procedure.

FIG. 1 shows the basic operating characteristics of an ion mobility spectrometer, such as the commercially available model MMS 160 Ion Mobility Spectrometer/Quadrupole Mass Spectrometer system (IMS/MMS) sold by PCP, Inc., West Palm Beach, Fla., under the trademark Phemto-Chem®. In this model the IMS is coupled to an optional quadrupole mass spectrometer through a 30µ aperture for further analysis under high vacuum of the ions from the IMS collector. The operation of such a device is well known and described in the literature, such as in the book Plasma Chromatography, edited by T. W. Carr, Publ. Plenum Press, New York 1984.

An IMS is a chemical vapor detector operating at atmospheric pressure. It can be used with a variety of gases, such as air, nitrogen, argon, helium, etc. A vapor sample can be introduced in many ways into the IMS, in which a radiation source, for example a nickel-63 β-radiation source in the MMS 160 IMS/MMS, ionizes the host gas at atmospheric pressure. This primary ionization initiates a sequence of ion-molecule interactions which lead to the formation of sufficiently energetic positive or negative ions which, in turn, ionizes the constituents of the vapor sample. All of the ions move downstream in the IMS cell under the influence of an applied voltage gradient and are separated in the drift region of the cell based on the unique drift times of the various chemical ion species, which generate the ion mobility spectrum.

An IMS utilizes a drift gas generally to provide a gaseous environment wherein the ions produced in the reaction region of the IMS in the carrier gas can drift with no change in identity which could arise from the continuation of ion-molecule reactions which have taken place in the reaction region of the IMS.

Humanity lives in a atmosphere containing a substantial amount of water vapor. Therefore, the most common and plentiful IMS interferant on earth is water. In extraterrestrial environments other vapors, such as methane or ammonia may be the most common interferant. Therefore, all references herein to water are meant to include other atmospheric IMS interferants, given the nature of the predominant atmosphere at the site of use.

Water vapor present in conventional IMS tends to react with the energetic ions extremely rapidly, such as within a millisecond, through ion-molecule interactions, thus precluding measurement of the energetic ions mobility in conventional apparatus and by conventional techniques.

Normally the energetic ions react quickly with the water to become the hydrated proton $(H_2O).H^+$. Therefore, the higher concentration of the water, the larger the value of n. This results in the problem that a large number of gaseous chemicals are not detectable, because their charge has transferred to water as the ionic product. In this water vapor the detectable product ions are those to which the positive charge is finally transferred from the hydrated water ion to produce the observed ion mobility spectrum.

Current IMS technology utilizes gases usually containing at least 10 parts per million of water vapor. This water concentration dominates the ion-molecule interaction sequence to produce in the positive ion mode, the water cluster reactant ion and the observed ion mobility spectrum. This water reactant ion does not tend to ionize some sample molecules that are intended to be detected, such as saturated hydrocarbons. Other chemical traces which could not be detected by the IMS were the ions of the so-called "energetic" ions, because as soon as they were formed, they quickly reacted to ionize less energetic gases, such as water vapor. For example, helium, oxygen, and nitrogen (which are the host gas components present at large concentrations) are some of the most energetic species due to the larger amount of the energy required to ionize these neutral molecules. Then the host gas ions quickly react with the lower concentration of water which would be normally present in the moist host gas. The water ions and water cluster ions interact with less energetic trace chemical species which have relatively low ionization potentials, or high proton affinities, to produce the trace chemical ions seen usually in the normal standard ion mobility pattern. Thus in normal, standard IMS the water ion is the reactant for these lower energy chemicals.

In view of the ubiquitous presence of water in the atmosphere, water vapors are the most common interferant in ion mobility spectrometry. Water, however, is not necessarily the only interferant. Under particular circumstances, other interferants could be any neutral species present in an excessive amount, such as oxygen, hydrocarbons, etc. As a rule of thumb, any species in excess of 0.1 ppm can interfere with the measurement of trace gases which are present the concentration of pans-per-billion and lower. Therefore, while reference is made herein generally to water since it is the dominant example of interferants, and since depending on its concentrations also the most simply measurable target species, such reference is also intended to include all other interferants, particularly those which are present in concentrations of 2 and more orders of magnitude higher than the concentration of the trace gases to be detected.

In conventional IMS technology, even when taking the best precautions, it is difficult to obtain gases with a total impurity level of 1 part per million. Therefore, a total impurity of 1 part per million is considered "ultra-pure" in IMS of current common commercial designs. The lifetime of an ion which is required to produce a mobility peak is in the order of magnitude of 10 to 20 milliseconds, or longer. This lifetime can be obtained by reducing the concentration of any would-be neutral reactant interferant to a level where a negligible amount of its product ion is formed. If, however, the would-be reactant is water, then its concentration in IMS must be at or below low parts per billion range to be not seen in the ion mobility pattern. With the method and means of this invention such conditions have been constructed and observed.

BRIEF DESCRIPTION OF THE INVENTION

It is a principal objective of the present invention to provide an IMS method and apparatus enabling the detection and measurement of energetic ion species and their quantitative measurement at atmospheric pressure through their drift velocity and mobility in an electric field. This is principally accomplished in accordance with the present invention by providing a considerably reduced water vapor concentration in the IMS technique, thereby to extend the lifetime of the energetic ion species to a value of typically in excess of about 15 milliseconds to enable their separation and identification.

By the use of a very dry gas sample, there is only a very low concentration of water molecules present, and therefore the secondary energetic ions from the trace gases have a lifetime of more than approximately 10–15 milliseconds availability during which their identity is preserved. The secondary energetic ions are separated and detected in the IMS sensor, and are quantitatively measured, by virtue of their velocity or mobility in the electric field therein.

Accordingly, the present invention relates to a hermetically contained ion mobility spectrometer which is interference-free (dry) utilizing a drift gas for the determination of trace analyte contaminants in an interference-free (dry) carrier gas, including a container for a sample gas containing an analyte, the concentration of which is to be determined, means for purifying which removes interferences such as water as well as the analyte from the sample gas to produce the carrier gas from it, the means for purifying being hermetically connected from the container through a metallic pipe, a source for the drift gas which may be the same or different than the carrier gas, an ion mobility spectrometer sensor having a carrier gas entrance and a drift gas entrance and a gas exit, the ion mobility spectrometer sensor being hermetically connected by a metallic pipe from the purifying means and from the source of the drift gas, a back diffusion trap being hermetically connected from the gas exit, and a signal readout being electrically and hermetically connected from the ion mobility spectrometer sensor for electrically sensing and displaying signals obtained in the sensor.

The invention further relates to a process for determining the concentration in gases of gaseous trace contaminants, which comprises purifying under hermetic circumstances a sample gas that contains the trace contaminants as well as analytes to convert it into a substantially water-free and analyte-free carrier gas, mixing the carrier gas with the sample gas, introducing under hermetic conditions the carrier gas-sample gas mixture into an ion mobility spectrometer sensor, introducing a substantially water-free drift gas into the ion mobility spectrometer sensor, determining the trace contaminant concentration of the sample gas, and venting the ion mobility spectrometer sensor.

When it is desired to observe the continuing ion-molecule reactions, as in the present case of ultra pure gas, because the resulting pattern contains both additional sample identity and quantity information, in accordance with the present invention, the drift gas is suitably identical to the carrier gas. If the drift gas does not contain the neutral reactive specie (i.e. water) then the ion will form a sharp peak. If water is present in the drift gas, then the ion can react to form a broadened peak, have a tail attached to the peak, or form a second peak, depending upon the water concentration. Since there is always some water present even in the case that one would refer to as "dry", there will be a situation where the valley between peaks involving the water reaction will not go to the baseline. This effect can be useful for the measurement of the water concentration in the sample gas which fills the entire IMS sensor. Other analytes and potential interferences may participate in the continuing ion-molecule reactions and produce mixed molecule ion combinations which survive to appear in the ion mobility spectrum, in many cases.

DESCRIPTION OF THE DRAWING

The invention is further described hereinafter with reference to the accompanying drawings, wherein.

DETAILED DESCRIPTION OF THE INVENTION

Figure 2:
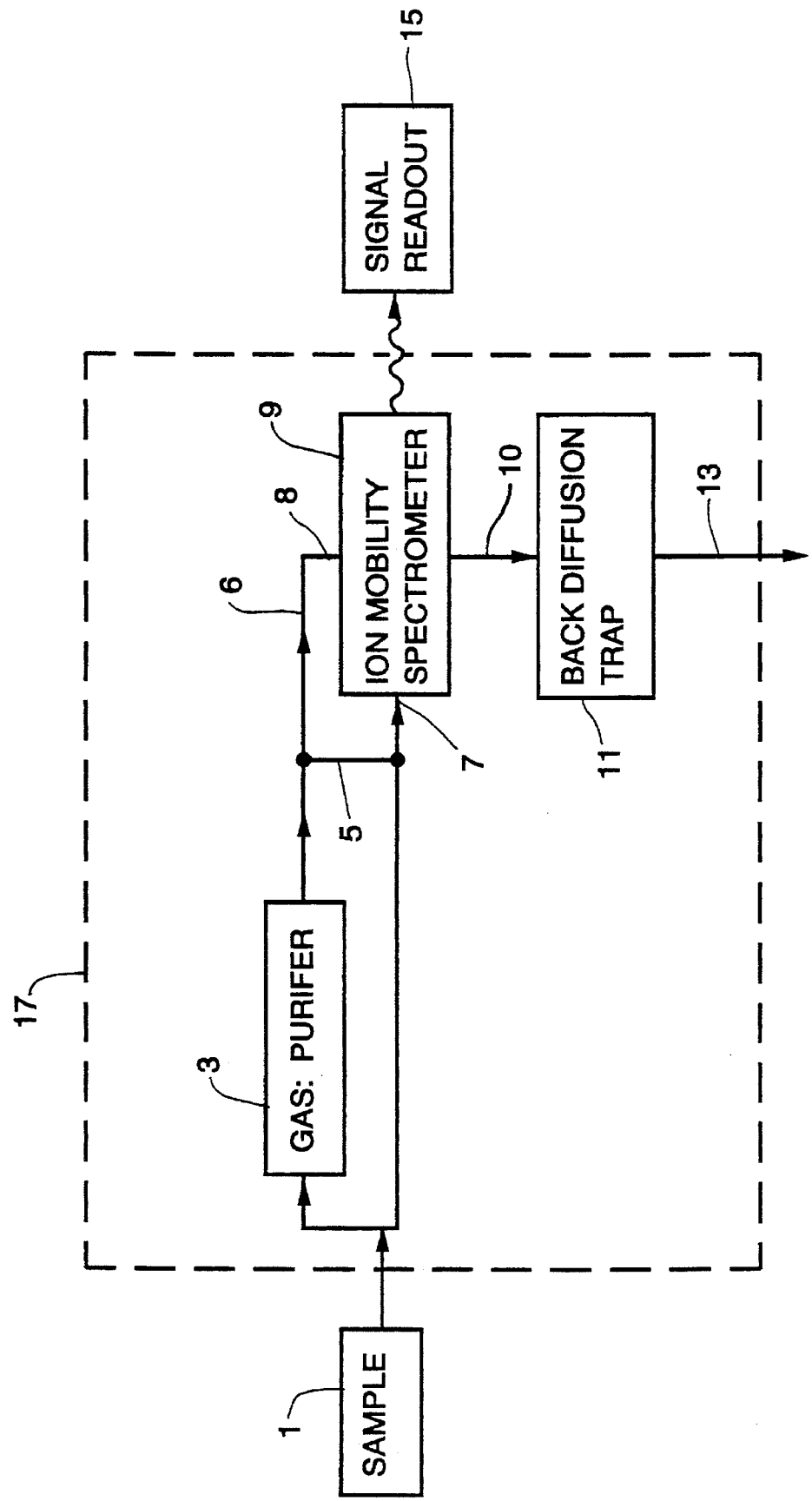
FIG. 2 is a schematic illustration of an IMS system accordance with the present invention.

A schematic diagram of a simple ion mobility spectrometer according to the present invention is shown in FIG. 2, which is an arrangement for measuring the low water and oxygen contamination levels in a bulk of very pure argon sample gas. The objective is to measure substantially continuously the purity of the argon gas. These water and oxygen contaminants of the argon may be typically 10 parts per billion by volume or less. The argon sample 1 is purified, or dewatered in a purifier 3. The resulting purified gas is used both as a carrier gas 5 and a drift gas 6. The carrier gas 5 is mixed with the argon sample gas, and the mixture is introduced into a hermetically sealed IMS sensor. The carrier gas 5 and the drift gas 6 are purer than the sample gas 1 because these gases have already passed through the gas purifier 3. The drift gas is introduced into the IMS sensor 9 through a drift gas inlet 8.

All of the gas is vented through an exit port 10 of the IMS through a back diffusion trap 11 which prevents moisture, oxygen, and other contaminants from diffusing upstream against the gas flow. All of the gas is vented through a final exit 13 into the atmosphere. A signal readout 15, such as a signal averager sold by Princeton Applied Research under Model No. 4203, provides the concentration of the trace water/oxygen, etc. in a conventional manner. The obtained signals can be recorded in a computer, suitably using an ASPB-1 advanced signal processing board and associated rapid data acquisition software. The plumbing is fabricated from stainless steel and is preferably treated by electropolishing and baking to reduce trapped water. The plumbing is preferably operated above ambient temperature to reduce water absorption and should suitably be adapted to be heated to a high temperature to reduce the outgassing of the walls during subsequent measurement after the walls are cooled. Outgassing can suitably take place at 200° C. or higher.

The apparatus can be suitably housed in a secondary, semi-sealed outer enclosure which is purged suitably with the exit gas from the final exit 13 to reduce leakage of interfering gases into the apparatus if there happens to be an inadvertent leakage.

Leakage can be tested by injecting a chemical, such as a testing gas, for example freon, methyl chloride, or acetone to determine whether it crosses any boundary that is supposed to be impervious to it.

One example of such leak detection is the use of the well-known commercial helium leak detector, wherein the helium test gas is detected with a mass spectrometer tuned to helium. The vacuum-tight envelope is coupled by vacuum plumbing to the mass spectrometer which acts as a vacuum pump. From the outside, a small helium gas jet (which is a very small constituent of the atmosphere) is swept over the vacuum envelope. If a leak is present in the envelope, the helium replaces the air leaking into the envelope and is seen as an increase in the $He^+$ ion peak in the display of the mass spectrometer. The maximum amplitude of the $He^+$ response in the mass spectrometer occurs when the helium gas jet is directly at the leak, which pinpoints the location of the leak.

When using the IMS for leak testing and for example using nitrogen as the IMS test gas, a fraction of the flowing gas is connected to an IMS. In the absence of a leak, the IMS response pattern is characteristic of pure nitrogen gas. If a leak develops or if present, oxygen and water from the atmosphere may enter the system and the IMS pattern changes. This result tells of a leak, but not where it is, because oxygen and water from the air may enter anywhere along the entire gas line. If a jet of chemical vapor which is not present in air, such as a light hydrocarbon, chlorofluorocarbon or even a very volatile light liquid such as methyl chloride, etc., is placed adjacent to the leak, the IMS detects it similarly to the helium leak detector operation but without the need for the vacuum arrangement. The position of maximum IMS response along the line will identity the position of the leak.

Where the sample gas 1 is sufficiently pure, it can be directly introduced to the IMS sensor through the gas inlet 7, without intermediate purification and without separately creating carrier and drift gases. This is the least expensive form of installation.

Figure 3:
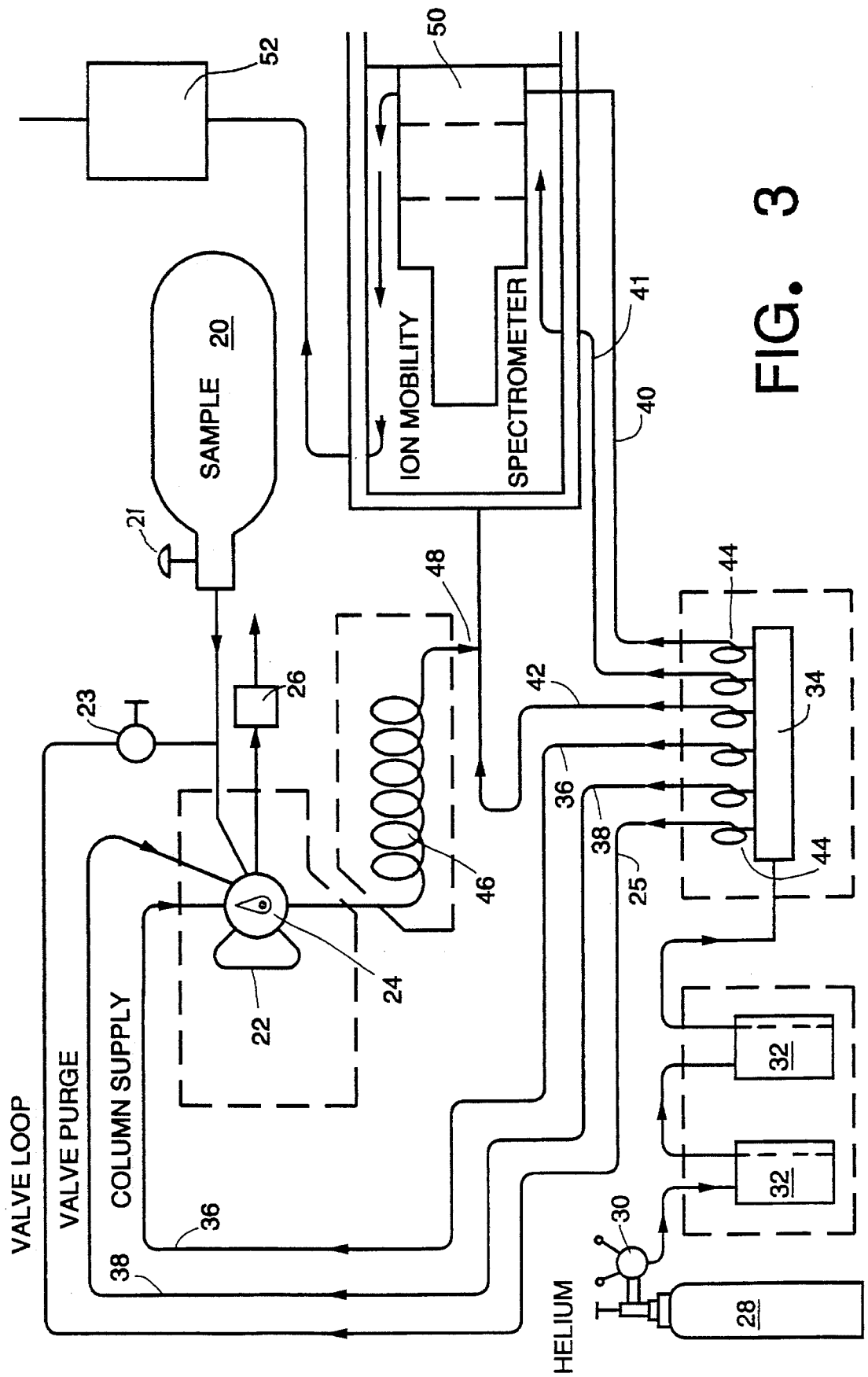
FIG. 3 is a schematic illustration of a more complex IMS system in accordance with the present invention.

In another embodiment of the apparatus of the present invention, as shown in FIG. 3, the chemical interferant, such as in the illustrated embodiment water and oxygen, is removed from the sample gas mixture containing the analyte (methane, or a chlorofluorocarbon in the illustrated embodiment) by combination of the IMS with a gas chromatograph. The retention time for oxygen is usually short in the GC column and the oxygen can be vented before the targeted analytes reach the IMS. Thus with the GC column potential interferents can be either vented or trapped on the GC column in order to prevent their entrance into the IMS. A tank 20 containing the sample gas mixture is connected through a tank closure valve 21 to a suitable 40 µl sample loop 22 that is connected to a sample valve 24, and can be vented through a back diffusion trap 26 to the atmosphere. The sample valve 24 is suitably a Carle Micro-Volume, 6 port, 2 position valve, suitably wrapped along with the sample loop and all connecting lines in insulated electric heating tape and suitably heated to approximately 100° C.–125° C. for sample introduction. The back diffusion trap is to prevent the entry of atmospheric moisture as an interferant out of the sample loop and the associated plumbing. The sample tank 20 is connected through a valve loop closure valve 23 to a valve loop 25 which sample valve 24 and its associated plumbing circuits. During operation of this apparatus the tank closure valve 21 is open, and the valve loop closure valve 23 is closed.

A regulated pressure gas tank 28 contains e.g. helium which is to be used as the IMS carrier gas, suitably at 90 psi, and as the IMS drift gas, as well as for purging the system between samplings of the analyte gas. The helium used in this embodiment of the invention passes through a two-stage pressure regulator 30 to a gas purification assembly 32, such as all brazed metal pre-baked canisters of a molecular sieve (e.g. a 13x molecular sieve) and activated charcoal. The canisters of the purification assembly 32 are suitably adapted to be refrigerated such as by immersion into liquid nitrogen or dry ice, for improving their water removal capability. The molecular sieves are suitably installed in a styrofoam insulated metal tub filled with dry ice in alcohol refrigerant. The purification assembly can also include a getter such as heated zirconium not only to ensure a low level of water interferant content of the gas, but also a low level of hydrocarbon interferants in the helium gas, down to a level of fractional parts per billion.

The purified helium passes from the purification assembly to a manifold 34. The gas supply lines from the sieve canisters can be suitably wrapped with two separate beaded heater wires and then insulated and connected to a variable electric source. The manifold splits the gas flow to supply the valve loop 25, a gas chromatograph supply line, a sample valve purge line 38, an IMS drift gas line 40, a cell purge gas line 41, and an IMS carrier gas line 42. Fixed gas flow restrictors 44, such as of fine stainless steel capillary tubes joined by high temperature alloyed copper brazing, are inserted between the manifold 34 and the various gas lines 25, 36, 38, 40 and 42 exiting from it. These materials which are suitably also employed for other plumbing of the system of the present invention, permit dewatering by baking of the manifold and all other plumbing components. Other gas flow restrictors, such as commercially available micrometer valves, or simple 1/16", 0.020" I.D. stainless steel tubing with 0.018" wire inserts, flattened to pass the desired flow, can also be employed. The flow restrictors are suitably also heatable from their exterior by means of removable electric heater.

The flow rates are suitably adjusted as shown in the following table:

TABLE 1

| Carrier | 100 ml/min |
|---|---|
| Drift | 490 ml/min |
| Purge | 175 ml/min |
| Valve loop | 23 ml/min |
| Valve purge | 8.5 ml/min |
| GC column | 30 psi head pressure |
| GC column flow | 13.9 ml/min |

The sample valve 24 switches the sample loop 22 from the flow circuit of the sample gas tank 20 to the circuit of the gas chromatograph supply line 36. In one position of the sample valve 24 an about 10 ml/min sample loop flow through the open valve loop closure valve 23 keeps the sample loop 22 flushed clean of the previous sampling. At the same time a gas flow of about 20 ml/min passes through the gas chromatograph supply line 36 and the sample valve 24, through a gas chromatograph (GC) column 46. Furthermore, a positive valve purge flow of about 15 ml/min is used to prevent atmospheric interferants from entering the pure helium gas in the unlikely case of a leak during operation of the sample valve 24. The sampling valve is suitably also adapted to be baked for degassing.

When the valve loop closure valve is closed, and the tank closure valve is open, the valve loop is filled within a few seconds with the next sampling of the analyte sample gas from the tank 20. After the sample loop 22 is filled, the tank closure valve is closed, and the sample valve 24 is turned to its second position. This connects the sample loop 22 to the GC column 46 where the analyte and interferant gas species of the sample are separated in a manner known per se from gas chromatography. A typical column of 1/16" diameter can be suitably packed with 2,6-dichlorophenyl isocyanate on 100/150 Porasil C. The material of the GC column is selected for retarding the undesired interferents, such as water. The targeted analytes which first exit the GC column, reach a junction 48 where they join with the purified carrier gas from the IMS carrier gas line 42, and pass into an IMS cell 50 suitably operated at 100° C. A mass spectrometer coupled to the IMS cell 50 can be used to monitor for any leaks in the system.

The pipe fittings are suitably provided with brazed and heliarc seals to assure the most gas tight connections. Nonbrazable fittings, such as inlets or outlets, suitably employ metallic compression type O-ring seals. Electrical feed-through connectors on housing are welded to the housing body.

The interior IMS cell 50 structure may be is suitably wrapped in a polytetrafluoroethylene sold under the trademark Teflon to help the cell to clear faster to produce better GC peaks, and glass/mica insulators sold under the trademark MACOR may be suitably employed as spacers between the drift and ionizing regions of the IMS cell, also to improve the speed of response to GC sample peaks.

The interferant water content of the sample gas is retarded in the GC column 46 and can enter the junction 48 minutes or even hours after the analyte passed through it. The delayed water content passes through the IMS 50 separately from the targeted analytes. The sample valve 24 and the sample loop 22 are purged and readied for a next sampling, as the gas from the gas chromatograph supply line 36 passes through the valve and the sample loop.

The water peak appearing in the GC column 46 can also be eliminated by back flushing the GC column in a manner known per se, through appropriate plumbing (not shown). The GC column 46 can also be rid of the water by diverting the gas flow of the column through a trapped vent (not shown) before the water peak can join the carrier at the junction 48. The rate of venting of the water from the GC column can be accelerated, and thus the water retention time can be reduced by raising the column temperature. The IMS can be suitably vented through a back diffusion trap 52 to prevent ambient interference. Suitably, the IMS and the associated plumbing can be disposed within a secondary enclosure (not shown) enabling the location of residual leaks.

Each type of analysis, involving specific analytes and interferants, may require specific modifications in the conditioning of the gases involved, however, the apparatus shown in FIGS. 2 and 3 represents the most frequently employable arrangements. The present invention thus enables the creating and analysis of the very driest, interferant free energetic ions for IMS analysis, down to fractional parts per billion contamination.

Figure 4:
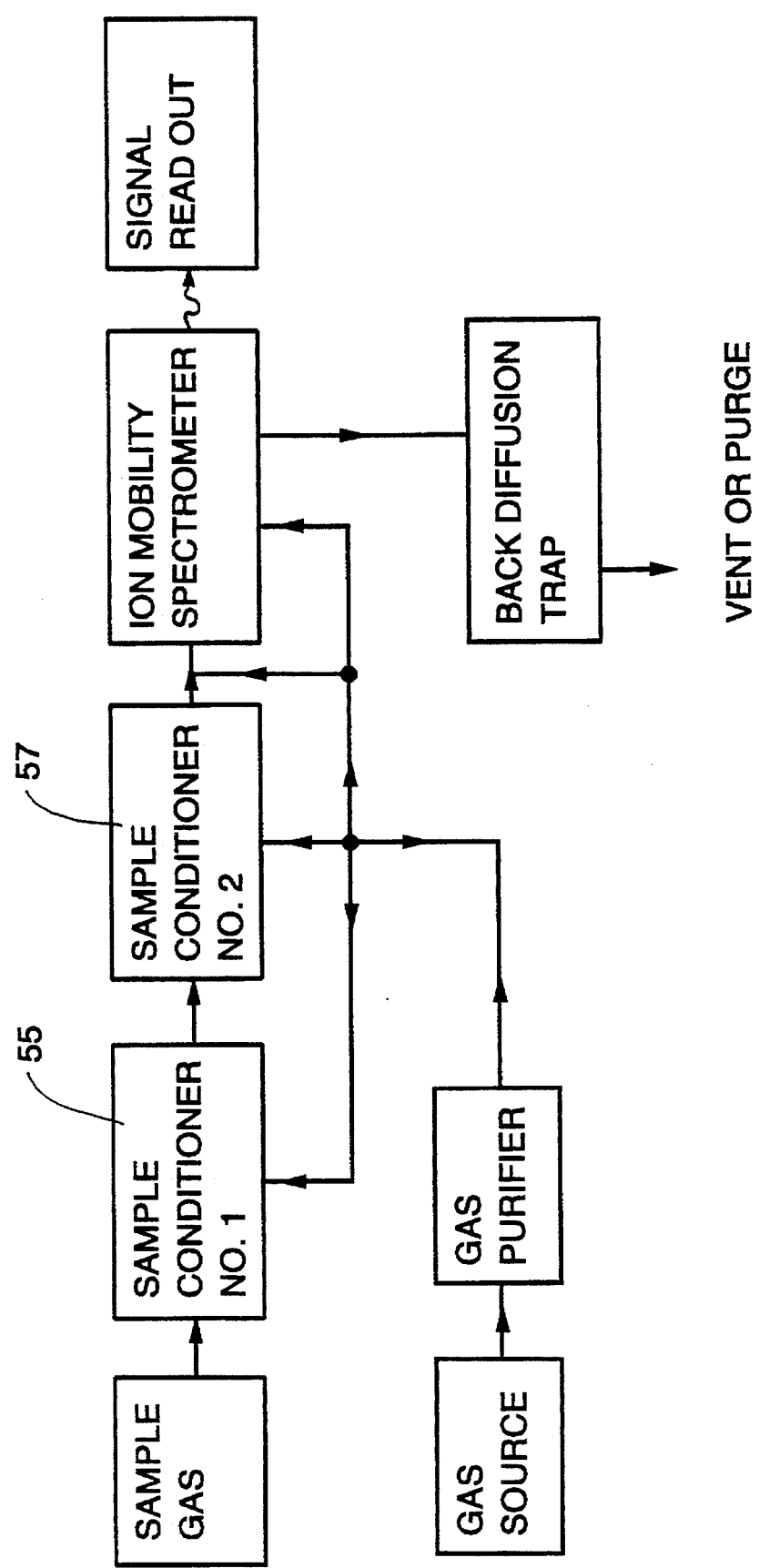
FIG. 4 is a generalized schematic illustration of various options of connecting apparatus in accordance with the present invention.

A generalized case of the arrangement of the system of the present invention is shown in FIG. 4, wherein a sample gas is passed through a first sample conditioner, and a second sample conditioner. The first sample conditioner separates the water and other interferants from the target sample, and the second sample conditioner separates the target analyte species from the remainder of the sample gas.

The following Table 2 outlines different sample parameters and identifies various components used in the schematically represented apparatus in FIG. 4. An example specified in Table 2 with reference to the arrangement of FIG. 4, is the analysis of light hydrocarbons in an environmental air sample. This can be done with the IMS, only in accordance with the present invention. The sample air of the example contains a mixture of hydrocarbons, moisture, oxygen, nitrogen and other organic matter shown in line 14 of the Table as "ES". In the example in the Table the #2 Sample Conditioner contains a sample trap and a gas chromatograph. The trap, suitably a cryogenic trap (CT), collects the targeted sample components and undesirable interferants, such as water. Low molecular weight hydrocarbons are chosen in the analysis as the targeted chemical. The trap of the example is a cold trap, such as a 0.1 cm diameter and 10 cm long tube filled with a 13X molecular sieve, cooled to the $-196°$ C. temperature of liquid nitrogen. This will trap and effectively hold the low molecular weight hydrocarbons and also water and higher boiling chemicals. After these hydrocarbons in the sample were collected for a known period of time from a known air flow, they are flash heated to gasify them and introduce the gas into the gas chromatograph (GC) with the required separation properties. For effective separation of the volatile hydrocarbons a short retention time is selected for them, and a longer retention time applies to the water content of the gas and the less volatile organics.

The targeted chemical exiting more rapidly from the gas chromatograph is then trapped in a second trap of a second sample conditioner, which is similar to the one described above. The water and other chemicals that were retained longer in the gas chromatograph exit later therefrom and can be vented into the atmosphere instead. Then the second trap is flash heated and its gasified contents are introduced into a second gas chromatograph for further purification if needed, by further separation of the targeted chemicals by their retention times, and from there into the IMS detector which identifies and quantifies the targeted components. In this manner the first sample conditioner separates and retains the water content (thus drying the sample), and the second sample conditioner further sorts and dries, if necessary, the targeted chemicals for their quantitative identification in the ultra-dry condition into the IMS.

For larger samples, a preparative gas chromatograph can be used instead of an analytical one.

After the measurement of several samples the column can be regenerated by backflushing to get rid of the retained water which may raise the water background into the IMS.

TABLE 2

Figure 1:
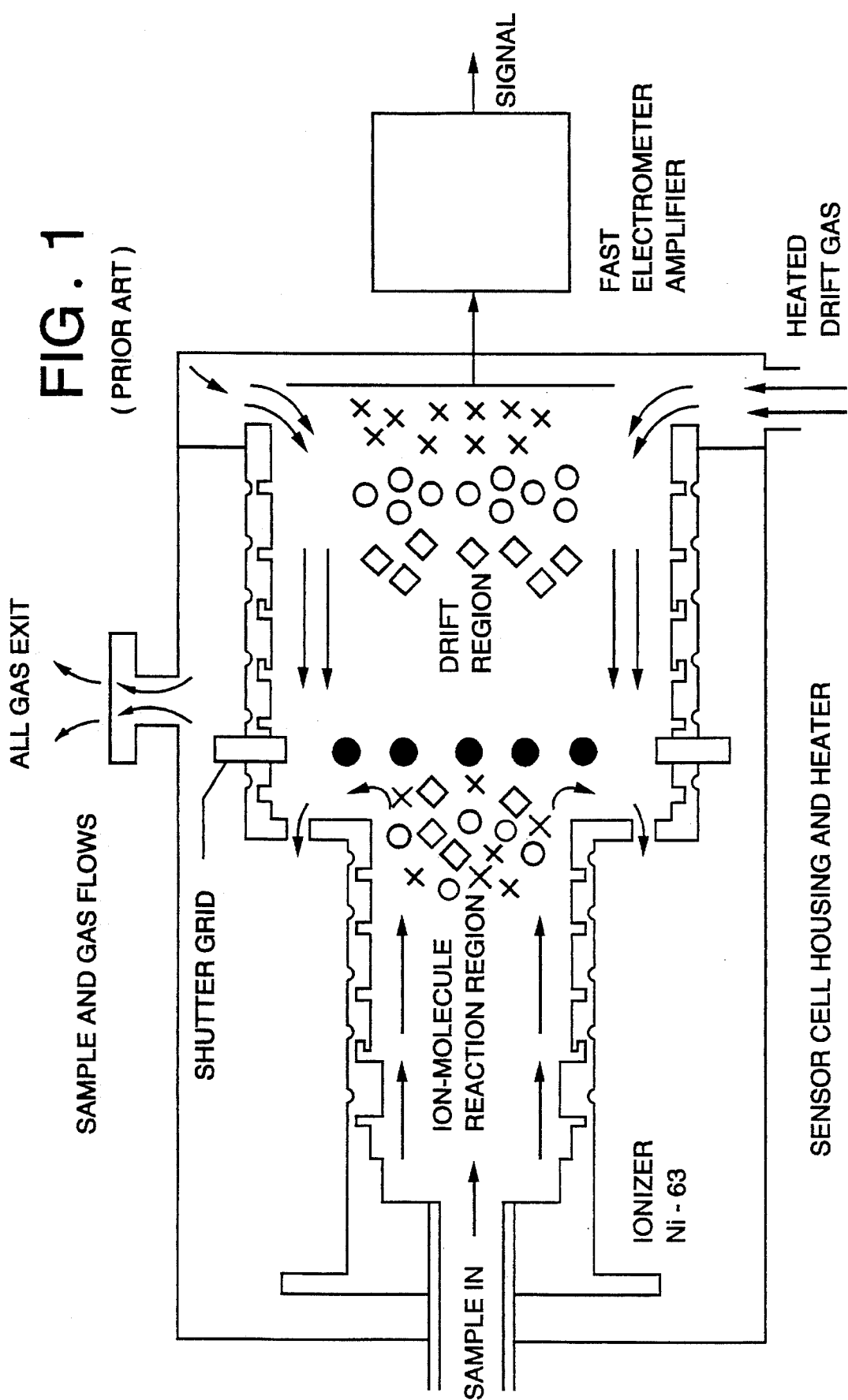
FIG. 1 is a schematic illustration of an ion mobility spectrometer.

| Sample Remarks | No.1 Sample Conditioner | No.2 Sample Conditioner | |
| --- | --- | --- | --- |
| UPG | none | none | FIG. 1 |
| UPG | none | SL/SGC | FIG. 2 |
| UPG | none | PGC | none |
| UPG | none | FGC | none |
| UPG | none | CT | none |
| Headspace | none | CT | none |
| TPS | none | CT | none |
| ES/other | none | CT | none |
| UPG | none | CT/SGC | none |
| Headspace | none | CT/SGC | none |
| TPS | none | CT/SGC | none |
| ES/other | none | CT/SGC | none |
| UPG/Headspace | SGC; or | Repeat with | FIG. 3 |
| TPS/ES | PGC; or and/or | CT/PGC | |

TABLE 2-continued

| other | FGC | CT/FGC |
| --- | --- | --- |

SYMBOL KEY

| CT | Cryogenic Trap |
| --- | --- |
| ES | Environmental Gaseous Sample |
| FGC | Frontal Analysis Gas Chromatograph |
| HPLC | High Pressure Liquid Chromatograph |
| LC | Liquid Chromatograph |
| PGC | Preparative Gas Chromatograph |
| SGC | Standard Gas Chromatograph (analytical) |
| SL | Sample Loop |
| TPS | Temperature Programmed Sample (evaporated from a solid surface, e.g. a silicon wafer) |
| UPG | Ultra Pure Gas |

$196°$ C. temperature of liquid nitrogen. Materials boiling above $100°$ C. can suitably be trapped at $0°$ C.

When the cryogenic trap is rapidly heated the cooled and the compressed sample amount rapidly evaporates in a burst to be injected into the gas chromatograph. Since the gas chromatograph separates the sample on the basis of retention time, the shorter the sample injection, the better will be the separation of the component peaks. Even if no gas chromatograph is used, a pulse-type of injection into the IMS is also beneficial, because it improves the signal-to-noise ratio, particularly at very low sample concentrations.

Alternate choices for the first sample conditioner can be selected to suite the type of sample. When a liquid sample is involved, the first sample conditioner 55 can be a liquid chromatograph to separate the solvent from the solute, both of which can be subsequently volatilized. The first sample conditioner 55 can be a temperature programmed chamber for the evaporation of the volatiles, followed by a cooled adsorber for trapping the volatiles, and then chromatographing the desorbed mixture of chemicals and chromatographing them is the second sample conditioner 57. Such a cooled adsorber-desorber of the second sample conditioner 57 can be considered as the injector for the gas chromatograph part of that second sample conditioner.

We claim:

1. An ion mobility spectrometer in a hermetically sealed container utilizing a drift gas for the determination of trace contaminants, in a carrier gas containing water or other interferents, which comprises
    (i) a source for a sample gas containing an analyte the concentration of which is to be determined,
    (ii) means for purifying the sample gas to produce the carrier gas from said sample gas, said means for purifying being hermetically connected to said ion mobility spectrometer through a first outgassable metallic pipe,
    (iii) a source for the drift gas which may be the same or different than the carrier gas,
    (iv) an ion mobility spectrometer sensor having a carrier gas entrance, a drift gas entrance, and a gas exit, said ion mobility spectrometer sensor being hermetically connected by a second outgassable metallic pipe to said source of the drift gas,
    (v) a back diffusion trap hermetically connected to said gas exit, and
    (vi) a signal readout electrically and hermetically connected to said ion mobility spectrometer sensor for electrically sensing and displaying signals therefrom.

2. The ion mobility spectrometer of claim 1, wherein said source of drift gas is said means for purifying, and whereby the carrier gas and the drift gas are identical with each other.

3. The ion mobility spectrometer of claim 1, further comprising an outer enclosure for providing a substantially leakproof enclosure around the spectrometer.

4. The ion mobility spectrometer of claim 3, wherein said back diffusion trap has a gas exit, and the gas exiting from said gas exit is adapted to be dispersed within said outer enclosure for maintaining a positive pressure of said exiting gas within said enclosure.

5. The ion mobility spectrometer of claim 4, wherein said outer enclosure has means for introducing a leak testing gas into the enclosure.

6. The ion mobility spectrometer of claim 1, wherein said means for purifying the sample gas is a gas chromatography column for separating and retarding water from the sample gas, and for optionally venting it from said column.

7. The ion mobility spectrometer of claim 1, wherein said metallic pipes are degassable stainless steel pipes.

8. The ion mobility spectrometer of claim 7, further comprising heaters for degassing said stainless steel pipes, said means for purifying the sample gas, and said ion mobility spectrometer.

9. The ion mobility spectrometer of claim 7, further comprising cryogenic coolers with or without a molecular sieve, and with or without an activated charcoal trap for degassing said stainless steel pipes.

10. The ion mobility spectrometer of claim 7, further comprising a getter for reducing the water content of the sample gas.

11. The ion mobility spectrometer of claim 10, wherein said getter is a heated spongy zirconium metal.

12. The ion mobility spectrometer of claim 1, wherein said means for purifying the sample gas comprises means for removing water and optionally other undesired contaminants therefrom.

13. The ion mobility spectrometer of claim 12, wherein said means for removing comprises a gas chromatograph for differentially retaining components of sample gas therein.

14. The ion mobility spectrometer of claim 13, wherein said means for removing further comprises a cryogenic trap for capturing and concentrating sample gas introduced thereinto, and for rapid injection of the captured and concentrated sample gas into the gas chromatograph.

15. The ion mobility spectrometer of claim 1, further comprising a cryogenic trap for injecting gas into the ion mobility sensor.

16. A process for determining the concentration of a trace contaminant in a gas sample, which comprises purifying under hermetic conditions said gas sample containing the target gas and trace contaminants to convert it into a substantially water-free carrier gas, introducing the carrier gas under hermetic conditions into an ion mobility spectrometer sensor, introducing under hermetic conditions a substantially water-free drift gas into the ion mobility spectrometer sensor, determining the trace contaminant concentration of the sample gas, and venting said ion mobility spectrometer sensor through a purifying means to prevent back diffusion of water and other interferents from the atmosphere.

17. The process of claim 16, wherein said carrier gas and said drift gas are identical to each other.

18. The process of claim 16, wherein said purifying comprises passing the sample gas trough a gas chromatography column for separating and retaining therein the water vapor content from the remainder of the sample gas, and passing said remainder to said ion mobility spectrometer.

19. The process of claim 16, wherein said purifying comprises at least one of passing said sample gas through a cooled molecular sieve, a getter, and a gas chromatographic column to separate the water vapor content from the remainder of the sample gas, and passing said remainder to said ion mobility spectrometer.

\* \* \* \* \*

UNITED STATES PATENT AND TRADEMARK OFFICE
CERTIFICATE OF CORRECTION

PATENT NO. : 5,457,316
DATED : Oct. 10, 1995
INVENTOR(S) : Martin J. Cohen; Robert M. Stimac It is certified that error appears in the above-identified patent and that said Letters Patent is hereby corrected as shown below:

Col. 1, line 5, insert:

--This invention was made with Government support under contract number NAS2-1326 awarded by NASA. The Government has certain rights in the invention.--

Signed and Sealed this

Twenty-second Day of April, 1997

Attest:

BRUCE LEHMAN

*Commissioner of Patents and Trademarks*

*Attesting Officer*

UNITED STATES PATENT AND TRADEMARK OFFICE
CERTIFICATE OF CORRECTION

PATENT NO. : 5,457,316
DATED : Oct. 10, 1995
INVENTOR(S) : Martin J. Cohen; Robert M. Stimac; Roger F. Wernlund It is certified that error appears in the above-indentified patent and that said Letters Patent is hereby corrected as shown below:

Col. 1, Line 5, insert:

--This invention was made with Government support under contract number NAS2-13276 awarded by NASA. The Government has certain rights in the invention.--

This certificate supersedes Certificate of Correction issued April 22, 1997.

Signed and Sealed this

Fifteenth Day of July, 1997

*Attest:*

BRUCE LEHMAN

*Attesting Officer*  *Commissioner of Patents and Trademarks*